US005304168A

United States Patent [19]

Sun

[11] Patent Number: 5,304,168

[45] Date of Patent: Apr. 19, 1994

[54] REAL IMAGE/RED RAY PULSE AND BEEP TYPE AMBLYOPIA CURING DEVICE

[75] Inventor: Han-Jun Sun, Chung Ching, China

[73] Assignee: Pei-Chang Cheng, Taiwan

[21] Appl. No.: 21

[22] Filed: Jan. 4, 1993

[30] Foreign Application Priority Data

Jan. 9, 1992 [CN] China .......................... 92 1 08012.3

[51] Int. Cl.[5] .......................... A61F 9/00

[52] U.S. Cl. .......................... 606/4

[58] Field of Search .......................... 606/2, 3, 4, 5, 6

[56] References Cited

U.S. PATENT DOCUMENTS 4,068,932 1/1978 Ohta et al. .......................... 351/206
4,256,384 3/1981 Kani et al. .......................... 351/211
5,106,179 4/1992 Kamaya et al. .......................... 351/44

FOREIGN PATENT DOCUMENTS 1660697 7/1991 U.S.S.R. .......................... 606/4

*Primary Examiner*—Stephen C. Pellegrino
*Assistant Examiner*—Sonya C. Harris
*Attorney, Agent, or Firm*—Bacon & Thomas

[57] ABSTRACT

A real image/red ray pulse and beep type amblyopia curing device is designed to take into account the "Substitutive Suppressed Competition" theory and includes a main frame, a red ray projector, a real image projector, and an electronic circuit composed of a power supply circuit, a speaker circuit, a real image/red ray projector circuit, an oscillation circuit, a red lamp connected to the oscillation circuit, a real image lamp connected to the power supply, and a real image/red ray selector switch, in which the real image lamp is installed at the bottom of the real image projector, one or more lenses are installed at the front side of the real image projector to provide parallel rays for providing a steady real image, a non-transparent dot of preferably 3 to 8 mm in diameter is made at the center of the front surface of the lens or lenses, and the red ray lamp is installed within the red ray projector.

5 Claims, 3 Drawing Sheets

REAL IMAGE/RED RAY PULSE AND BEEP TYPE AMBLYOPIA CURING DEVICE

BACKGROUND OF THE INVENTION

1. Field of the Invention

The present invention relates to an electronic medical instrument, particularly a real image/red ray pulse and beep type amblyopia curing device.

2. Description of the Prior Art

Amblyopia is a children's eye disease with a relatively high incidence rate. Until now, no common agreement has been reached on the pathology and mechanism of this disease. Conventional theory holds that the disease involves a pathological change in the brain. The alternative "Traumatic Theory" is that amblyopia is caused by a pathological change not detectable by the normal means on the patent's retina. However, neither theory has been generally accepted today. The existing children's amblyopia curing devices are mostly designed on the principle that the retina's yellow spot cone cells are sensitive to red rays, such as the prior art amblyopia curing device which is composed of a red ray flickering circuit, a drawing circuit, a stereo music playing circuit, and a power supply circuit arranged so that the patient being cured can concentrate his mind on watching a plurality of conductor wires on a printed circuit and flickering red rays behind the conductor wires and tracing a pen along a pattern on the printed circuit placed beneath a transparent board under which red rays are flickering. However, such a device has the following disadvantages:

(1) Only the yellow spot are stimulated, the degree of stimulation is limited, and hence the curing effect is poor.

(2) Sophisticated structure and high production cost.

(3) A set of high intensity flickering red ray source is used without a converging mirror or light shield, hence serious diffusion occurs, electric power consumption is high, and the curing effect is poor.

(4) A lot of switches for control of the circuits is required, and hence operating procedure is complicated and use is not convenient.

SUMMARY OF THE INVENTION

As noted above, amblyopia is a children's eye disease with a relatively high incidence rate. But no common agreement has been reached on the pathology and mechanism of this disease, with the conventional theory being that the disease involves a pathological change in the brain, while the competitive "Traumatic Theory" holds that amblyopia is caused by a pathological change not detectable by normal means on the patent's retina. The present invention is based on the theory vision is transmitted in a plurality of channels, such as a yellow spot channel, i.e., X-channel, for fine resolution, and a peripheral channel, i.e. Y-channel, for a rough spatial structure and that when the X-channel and the Y-channel are opened simultaneously, the Y-channel makes a competitive suppression against the X-channel so that the nervous tissues at the periphery of the X-channel is suppressed to slow down visual signal transmission. Such a finding has been named the "substitutive suppressed competition" theory.

The real image/red ray pulse and beep type amblyopia curing device according to the present invention, which is designed to take into account the "Substitutive Suppressed Competition" theory, includes a main frame, a red ray projector, a real image projector, and an electronic circuit composed of a power supply circuit, a speaker circuit, a real image/red ray projector circuit, an oscillation circuit, a red lamp connected to the oscillation circuit, a real image lamp connected to the power supply, and a real image/red ray selector switch, in which the real image lamp is installed at the bottom of the real image projector and one or more lenses are installed at the front side of the real image projector to provide parallel rays for providing a steady real image. A non-transparent dot of preferably 3 to 8 mm in diameter, is made at the center of the front surface of the lens or lenses, and the red ray lamp is installed within the red ray projector. A real image is projected to suppress the Y-channel, and then the red ray pulse is applied to stimulate the X-channel to improve the X-channel's strength, and consequently to cure the patient's amblyopia. The present invention is applied by first turning on the real image lamp to provide a steady real image of adequate intensity, and then causing the patient to stare at the real image for 45 seconds to release the Y-channel's competitive suppression against the X-channel. Then, a real image/red ray selector switch is turned to light the red ray lamp to provide a red ray pulse having a wave length of about 650 mm, an intensity 2.5 mcd and a frequency of about 15 Hz, while the speaker circuit is activated to generate a beep. The patient is required to stare at the lamp for seven minutes to stimulate the nervous tissue at the periphery of the X-channel to improve the patient's vision.

The present invention has the following features:

(1) A combination of real image and red rays to maximize the red ray's stimulation of the X-channel. Some clinical experiments have proven its effect on children of different ages, as follows:

| | Degree of Amblyopia | | | |
|---|---|---|---|---|
| EFFECT | Mild | Medium | Serious | Total |
| Number of Patients Cured | 11 | 39 | 2 | 52 |
| | 100% | 67.24% | 25% | 67.53% |
| Effective | | 18 | 4 | 22 |
| | | 31.03% | 50% | 28.57% |
| Non-effective | | 1 | 2 | 3 |
| | | 1.72% | 25% | 3.90% |
| Total | 11 | 58 | 8 | 77 |

(2) The real image lamp and the red ray lamp are located in respective projectors with lens to dispose of the rays to provide a steady real image and a highly intensive red ray to help the patient to concentrate on staring at the image and ray for the best therapeutic effect.

(3) Compact and simple structure, easy to operate and low production cost. It can be used at home directly.

BRIEF DESCRIPTION OF THE DRAWINGS

The invention, as well as its many advantages, may be further understood by the following detailed description and drawings in which.

DETAILED DESCRIPTION OF THE PREFERRED EMBODIMENT

Figure 1:
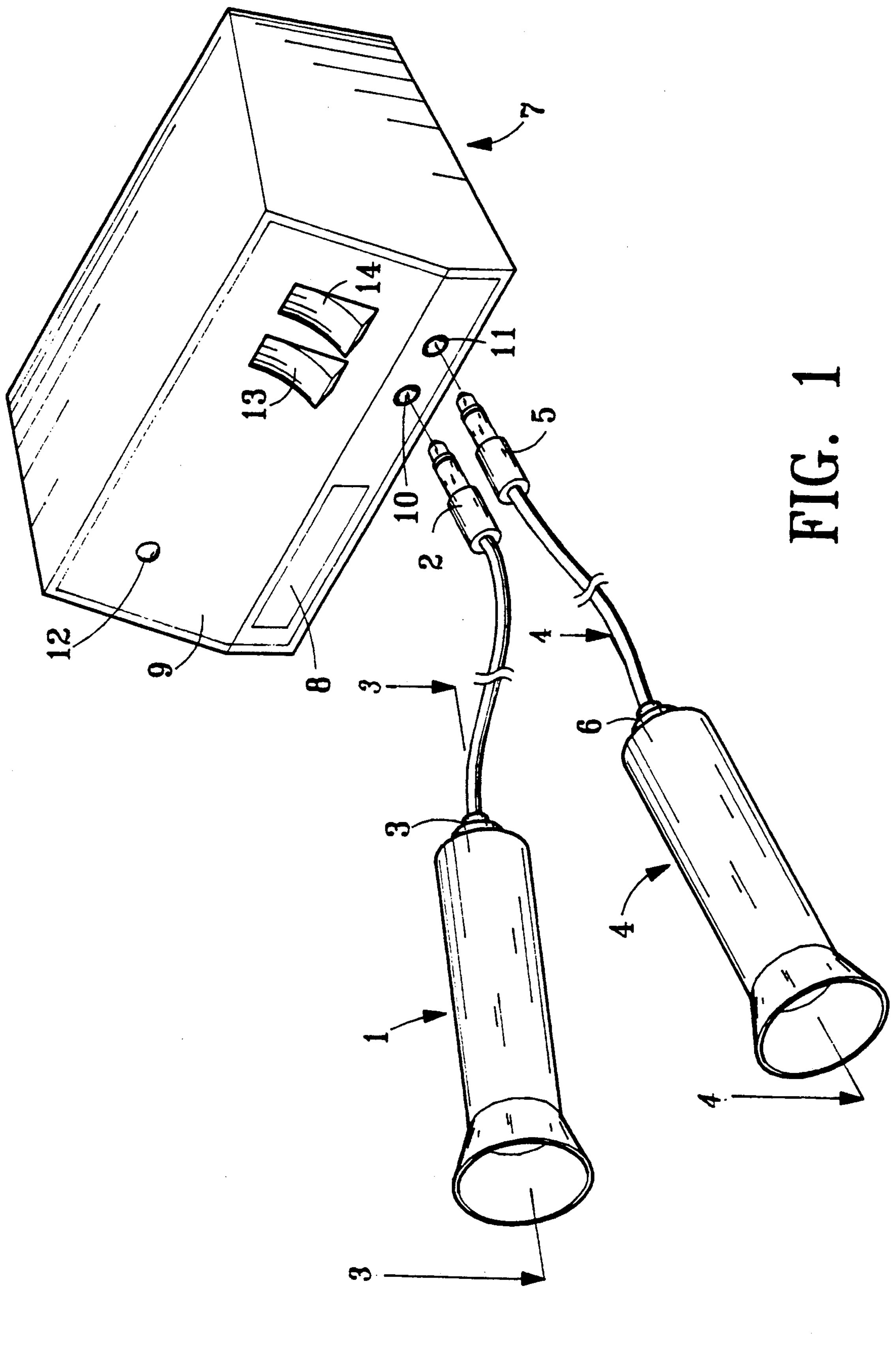
FIG. 1 illustrates a real image/red ray pulse and beep type amblyopia curing device according to the present invention.
Figure 2:
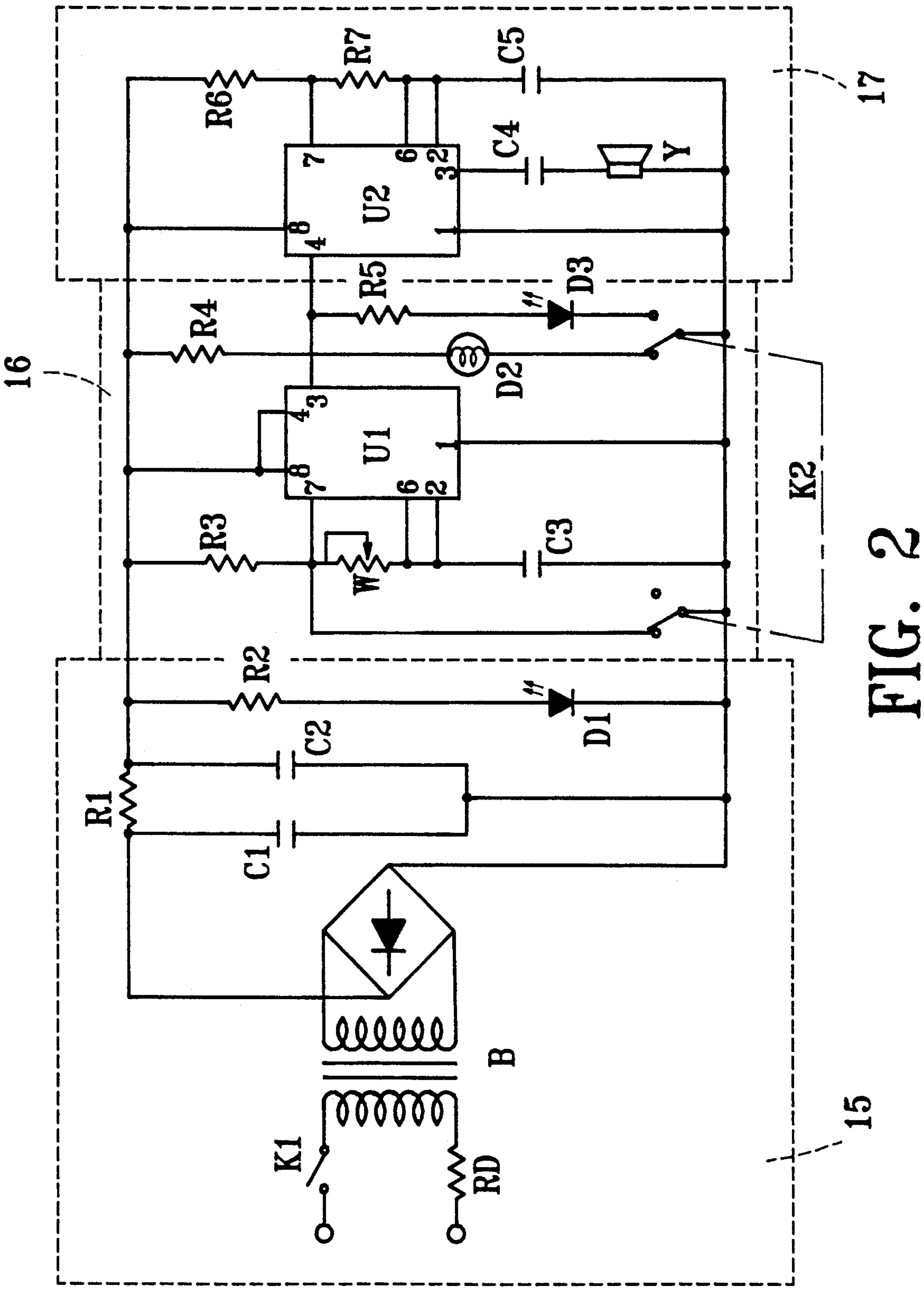
FIG. 2 is a circuit diagram for an embodiment of the real image/red ray pulse and beep type amblyopia curing device according to the present invention.
Figure 3:
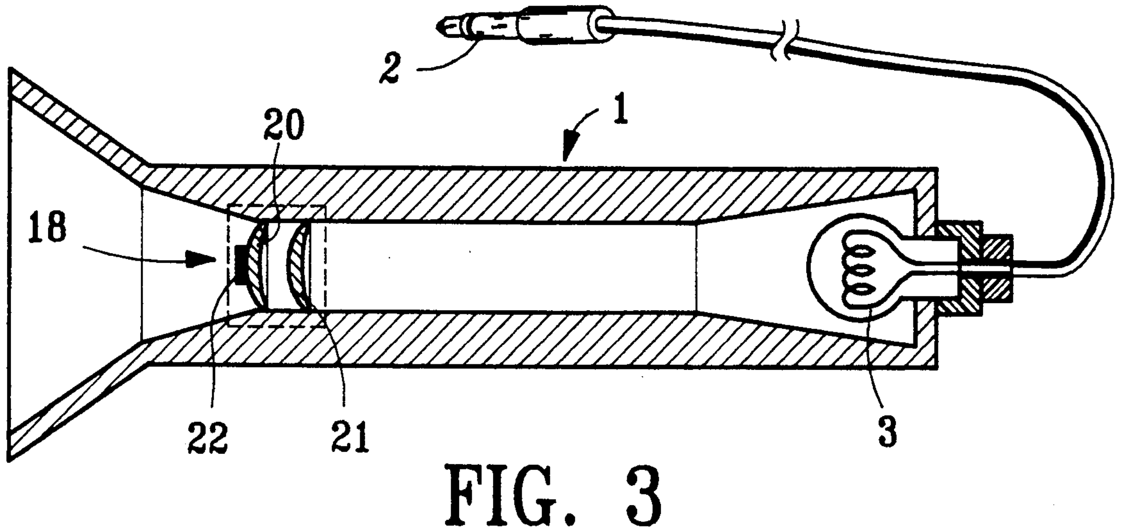
FIG. 3 is a sectional view taken along line A—A in FIG. 1.

Referring to FIGS. 1 thru 3, the amblyopia curing device according to the present invention includes a main frame 7, a real image projector 1, and an red ray projector 4. The main frame 7 includes a instrument panel 9 on which a nameplate is attached, and in which a real image projector socket 10, a red ray projector socket 11, an operating indicator (D1) 12, a power switch (K1) 13 and real image/red ray selector switch (K2) are incorporated. As shown in FIG. 2, there is a power supply circuit 15 within the main frame 7. The power supply circuit 15 is connected to a speaker circuit 17 via a real image/red ray projector circuit 16 which is composed of an oscillation circuit, a red lamp (D3) (which corresponds to element 6 in FIG. 1) connected to the oscillation circuit, and a real image lamp (D2) connected to the power supply and the real image/red ray selector switch (K2) (which corresponds to element 14 in FIG. 1). The oscillation circuit is composed of a resistor R3, a rheostat W, a capacitor C3, and a clock integrated circuit (U1). The red lamp (D3) 6 is connected to output pins of the integrated circuit (U1). The real image lamp (D2), which corresponds to element 3 in FIG. 1, is a 6.3 V incandescent lamp. When the power switch (K1) (corresponding to element 13 in FIG. 1) is at On position, the real image/red ray selector switch (K2) 14 is at a position as shown in FIG. 2, a 220 V alternate current is passing through a transformer where it is rectified and filtered to become a 12 V direct current output to light the indicator (D1) (corresponding to element 12 in FIG. 1) and the real image lamp (D2) 3. Lighting of the indicators (D1) 12 is to indicate that the device according to the present invention is working. At that time, since the real image/red ray selector switch (K2) 14 causes a pin 2 of the integrated circuit (U1) to become low, then another integrated circuit (U2) produces a continuous oscillation and consequently a speaker Y produces a continuous beep because of the action of resistors R6 and R7 as well as a capacitor C5. 45 or 90 seconds later, the real image/red ray selector switch (K2) 14 is turned to another position manually to turn off the real image lamp (D2) 3, and to cause the red lamp (d3) 6 to flicker and the speaker Y to produce a series of intermittent beeps, since the real image/red ray selector switch ((K2) 14 is turned to another position as shown so that the integrated circuit (U1) is oscillated at a cycle longer than that of the integrated circuit (U2) for the pin 4, the reset pin of the integrated circuit (U2) is connected to the pin 3 of the integrated circuit (U1) to receive two different potentials, high and low, alternately. Seven minutes late, the real image/red ray selector switch (K2) 14 is turned to the position shown to repeat the above procedure. After the above therapy, the power switch (K1) 13 is turned off to end the operation of the device according to the present invention.

As shown in FIG. 3, the real image lamp 3 is installed at the bottom of the real image projector 1. Two lenses are installed at the front side of the real image projector 1 to cause of rays emitted by the real image lamp 3 to become parallel rays in order to provide a steady real image with minimum difference in spherical mirror surfaces. To achieve the above purpose, two concavo-convex lenses 20 and 21 are used. The concavoconvex lens 20 preferably has a focal length of 25.42 mm and a diameter of 10 to 20 mm. The concavoconvex lens 21 is preferably having a focal length of 28.23 mm and a diameter of 10 to 20 mm. The distance between these two concavo-convex lenses is preferably 2 to 8 mm. If both the concavo-convex lenses are 14 mm in diameter, the distance between them is preferably 3 mm for the best therapeutic effect. A non-transparent dot of 3 to 8 mm in diameter is made at the center of the front surface of the concavo-convex lens 20.

Figure 4:
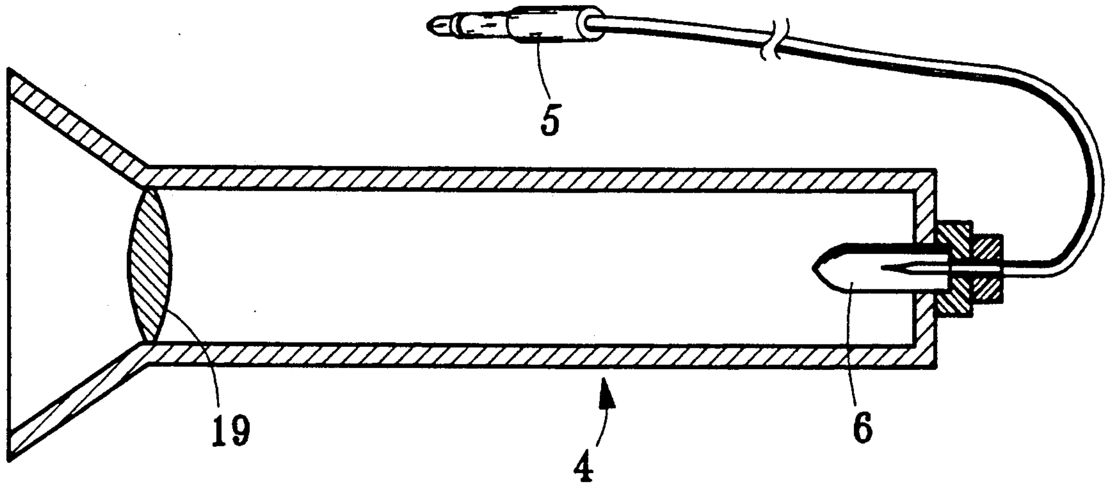
FIG. 4 is a sectional view taken along line B—B in FIG. 2.

As shown in FIG. 4, a convex lens 19 is installed at the front side of the red ray projector 4 to minimize patient fatigue due to prolonged exposure to the flickering red light.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. Apparatus for treating amblyopia, comprising: a red ray projector; a real image projector; and a main frame containing an electronic circuit to which lamps positioned in the red ray projector and real image projector are connected, said electronic circuit including a power supply circuit, a speaker circuit, and a circuit for energizing the respective lamps positioned in the red ray projector and the real image projector, said energizing circuit selectively connecting an oscillation circuit to the lamp positioned in the red ray projector and a power supply to the lamp positioned in the real image projector, said electronic circuit further comprising a real image/red ray selector switch, wherein the real image projector includes one or more lenses arranged to provide parallel rays generated by the lamp positioned therein for creating a real image of an object located at a center of a surface of the lens, the red ray lamp being installed within the red ray projector, said energizing circuit forming means for causing the real image projector to project a steady real image at which a patient stares for a predetermined period of time to release a Y-channel's competitive suppression against an X-channel in the patient's eye, said switch forming means for enabling the red ray lamp to be turned on to stimulate the nervous tissue at the periphery of the X-channel following said competitive suppression in order to maximize stimulation of the X-channel.

2. Apparatus as claimed in claim 1, wherein said object is a nontransparent dot of between 3 and 8 mm. in diameter positioned at a center of a front surface of said lens.

3. Apparatus as claimed in claim 1, wherein said lens system comprises two concave-convex lenses, one of said lenses having a focal length of 25.42 mm. and a diameter of 10 to 20 mm., and the other said lenses having a focal length of 28.23 mm. and a diameter of 10 to 20 mm., the distance between the lenses being approximately 2.8 mm.

4. Apparatus as claimed in claim 1, wherein the real image lenses comprise two concave-convex lenses, each having a diameter of approximately 14 mm.

5. Apparatus as claimed in claim 1, wherein the real image lenses comprise two concavo-convex lenses positioned at a distance of approximately 3 mm. apart from each other.

* * * * *